(12) United States Patent
Freund et al.

(10) Patent No.: US 7,356,124 B2
(45) Date of Patent: Apr. 8, 2008

(54) COLLIMATOR FOR A BEAM DETECTOR, AND A COMPUTED TOMOGRAPHY UNIT

(75) Inventors: Andreas Freund, Heroldsbach (DE); Gottfried Tschöpa, Rednitzhembach (DE)

(73) Assignee: Siemens Aktiengesellschaft, Munich (DE)

( * ) Notice: Subject to any disclaimer, the term of this patent is extended or adjusted under 35 U.S.C. 154(b) by 78 days.

(21) Appl. No.: 11/455,213

(22) Filed: Jun. 19, 2006

(65) Prior Publication Data

US 2006/0291617 A1    Dec. 28, 2006

(30) Foreign Application Priority Data

Jun. 20, 2005   (DE) ...................... 10 2005 028 411

(51) Int. Cl.
*G21K 1/02* (2006.01)
(52) U.S. Cl. ......................................... 378/147; 378/19
(58) Field of Classification Search ............. 378/4–20, 378/145, 147, 149; 250/370.08, 370.09, 250/505.1
See application file for complete search history.

(56) References Cited

U.S. PATENT DOCUMENTS 5,012,506 A    4/1991   Span et al. ................. 378/152

FOREIGN PATENT DOCUMENTS

| DE | 38 51 119 T2 | 8/1994 |
| DE | 197 50 935 A1 | 6/1999 |
| DE | 100 11 877 C2 | 8/2002 |

OTHER PUBLICATIONS

German Search Report.

*Primary Examiner*—Courtney Thomas
(74) *Attorney, Agent, or Firm*—Harness, Dickey & Pierce, P.L.C.

(57) ABSTRACT

A collimator is disclosed for a beam detector, having a number of juxtaposed collimator plates between which there is respectively arranged for stiffening the collimator, at least one supporting element that is constructed from a material transparent to X-rays and supports the collimator plates laterally. A computed tomography unit having such a collimator is further disclosed.

20 Claims, 4 Drawing Sheets

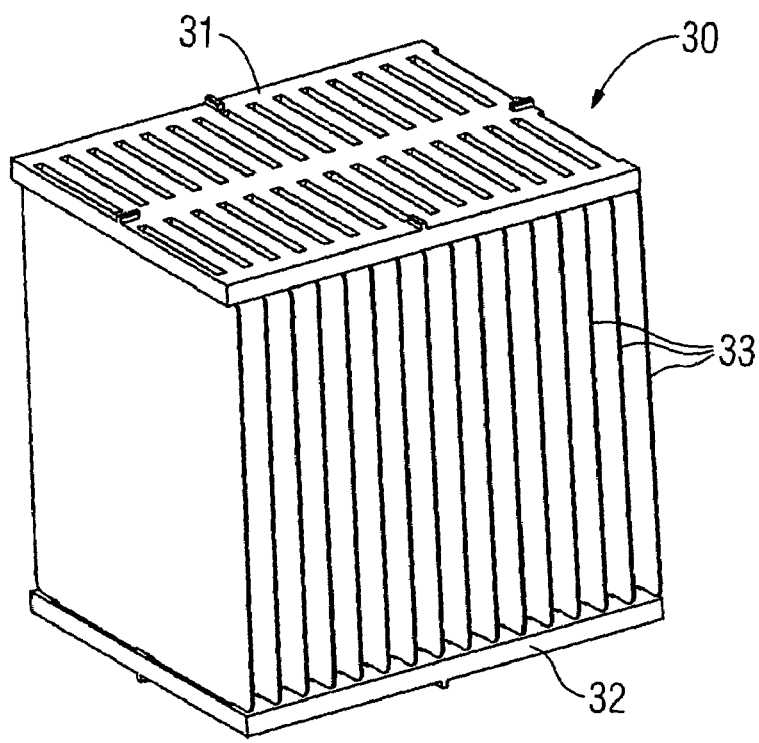
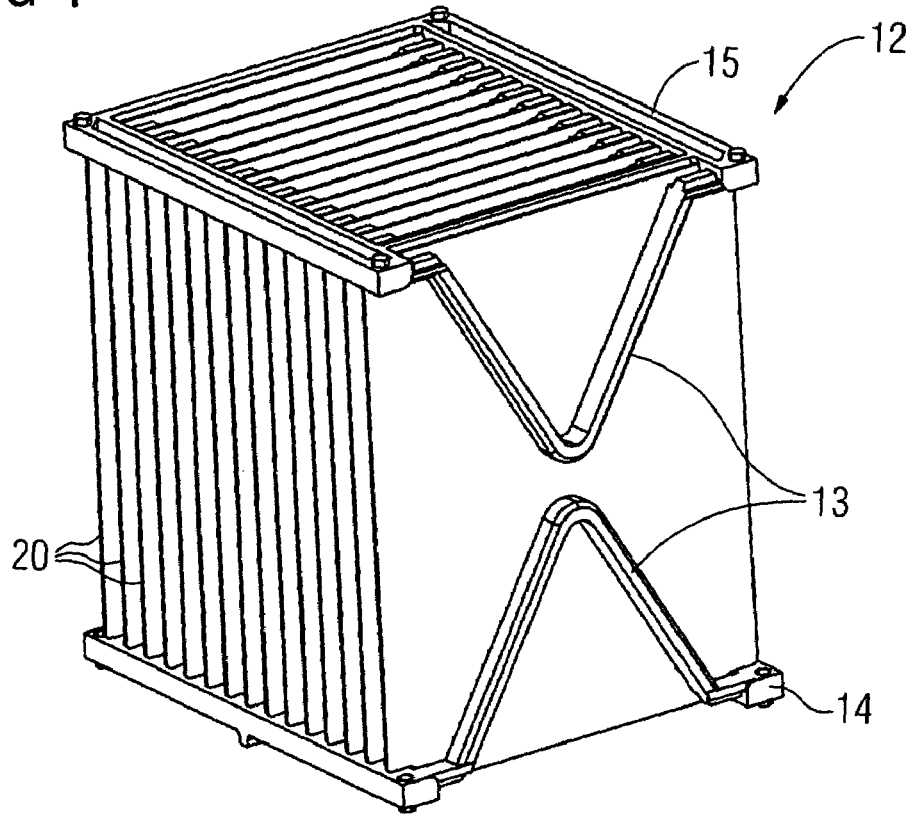

COLLIMATOR FOR A BEAM DETECTOR, AND A COMPUTED TOMOGRAPHY UNIT

PRIORITY STATEMENT

The present application hereby claims priority under 35 U.S.C. §119 on German patent application number DE 10 2005 028 411.6 filed Jun. 20, 2005, the entire contents of which is hereby incorporated herein by reference.

FIELD

The invention generally relates to a collimator for a beam detector, for example for an X-ray detector, having juxtaposed collimator plates. The invention also generally relates to a computed tomography unit having such a collimator.

BACKGROUND

A collimator is used, for example, when imaging with the aid of an X-ray machine, for example a computed tomography unit. Arranged on a rotary frame, the computed tomography unit has an X-ray system with an X-ray source and an X-ray detector. The X-ray detector is generally constructed from a multiplicity of detector modules that are lined up against one another in a row or in two dimensions. Each detector module of the X-ray detector includes, for example, a scintillator array and a photodiode array that are aligned with one another.

The mutually aligned elements of the scintillator array and of the photodiode array form the detector elements of the detector module. Arranged above each scintillator array in order to reduce influences of scattered radiation is a collimator which has the effect that only X-radiation of a specific spatial direction reaches the scintillator array. The X-radiation impinging on the scintillator array is converted into light that is converted into electrical signals by the photodiode array. The electrical signals form the starting point of the reconstruction of an image of an object being examined using the computed tomography unit.

The collimators of the detector modules of the X-ray detector have collimator plates that are aligned with the focus of the X-ray source of the X-ray machine, are fixed in plastic parts and are positioned relative to one another. The fixing of the juxtaposed collimator plates is performed on the top side and underside of the collimator. The detector modules with the collimators are arranged in a computed tomography unit on a so-called detector arc of the rotary frame. The detector arc is arranged opposite the X-ray source on the rotary frame, that is to say the rotating part of the gantry of the computed tomography unit.

The trend toward larger detector widths in the direction of a planar detector having a multiplicity of detector modules, as well as toward higher speeds of the rotating part of the gantry also leads to longer collimator plates. The problem arises here that as the detector arc rotates the collimators arranged at the ends of the detector arc are, in particular, acted upon by forces of such a nature that the collimator plates of these collimators are bent out of form as a consequence of the forces acting. This bending or deformation of the collimator plates can go so far that when an object is being examined these collimator plates cast an X-ray shadow and thus lead to image defects.

SUMMARY

It is therefore the object of at least one embodiment of the invention to specify a collimator and/or a computed tomography unit in such a way that bending or deformation of the collimator plates relative to one another is largely avoided.

According to at least one embodiment of the invention, an object may be achieved by way of a collimator for a beam detector, having a number of juxtaposed collimator plates between which there is respectively arranged for stiffening the collimator at least one supporting element that is constructed from a material transparent to X-rays and supports the collimator plates laterally. It is, therefore, proposed according to at least one embodiment of the invention to arrange a supporting element made from a material transparent to X-rays between two collimator plates in such a way that bending and deformation of the collimator plates relative to one another such as have occurred up to now during rotation of the collimators in a computed tomography unit are avoided. In this case, a collimator plate and a supporting element are alternately arranged using a type of stacking technique so as to produce a comparatively stiff design of the collimator, as a result of which, as already mentioned, it is possible to avoid bending or deformation of the collimator plates. A material that is transparent to X-rays is understood in this case as a material that does not have a negative effect on imaging with the aid of X-radiation, and so causes only a negligible attenuation of the X-radiation passing through an examination object.

According to an example embodiment of the invention, the supporting elements are interconnected in such a way that the collimator has a device comprising slots between the supporting elements, one slot each being present for holding a collimator plate between two supporting elements. The device having slots renders it possible in a simple way to arrange the collimator plates in a defined way relative to one another.

In accordance with one variant of at least one embodiment of the invention, the collimator has two devices with slots between the supporting elements for holding collimator plates, in which one device serves as base element and the other device serves as cover element. This embodiment of the collimator is used for example, in particular, whenever the collimator plates are of relatively large design such that a device having supporting elements no longer suffices to stiffen the collimator.

According to one embodiment of the invention, the slots are configured in such a way that in the event of arrangement over a beam detector the collimator plates arranged in the slots are aligned at least substantially with the focus of a radiation source assigned to the beam detector. One aim of this is to achieve that as far as possible only the radiation emanating from the radiation source and penetrating the examination object reaches the beam detector mounted downstream of the collimator.

Variants of embodiments of the invention provide that the supporting elements can be designed as supporting crosses, or else also be of U-, V- or W-shaped design. According to one example embodiment of the invention, the supporting elements may have at least substantially the same wall thickness in the direction of the radiation penetrating them so that the attenuation, which although reduced or even minimum is nevertheless present, of the radiation by the supporting elements and/or the device is substantially the same, and consequently image defects entailed by the arrangement of the supporting elements or the device in the beam path are largely avoided.

According to one example embodiment of the invention, the supporting elements may be made from a glass fiber reinforced liquid crystal polymer (LCP).

According to further variants of embodiments of the invention, the device having slots, which is a base element or a cover element, is an injection-molded part. According to one variant of an embodiment of the invention, for the purpose of stiffening the device having slots preferably has a support strut on the edge side and/or arranged between two supporting elements.

Furthermore, according to one variant of an embodiment of the invention, for the purpose of further stiffening the collimator the supporting elements are bonded to the collimator plates, the adhesive preferably being a low-viscosity adhesive.

In order to be able to arrange the collimator in the required way over a beam detector, it is provided according to one variant of an embodiment of the invention that the base element has at least one positioning lug for the purpose of positionally accurate arrangement over the beam detector.

Further variants of embodiments of the invention provide that the collimator plates have tungsten, molybdenum or tantalum, it being possible to construct the collimator plates completely from one of these materials or from an alloy containing one of these materials.

The collimator may, for example, be provided for an X-ray detector, in particular for a detector module of an X-ray detector constructed from a multiplicity of detector modules.

As a consequence of the inventive design of the collimator, such collimators can be aligned on all sides next to collimators of identical design, and are therefore suitable, in particular, as collimators for so-called planar detectors that are formed as a rule from a multiplicity of detector modules lined up one against another.

An object of at least one embodiment of the present invention also may be achieved by way of a computed tomography unit having an X-ray source and a beam detector fitted opposite the X-ray source. According to at least one embodiment of the invention, the beam detector is assigned a collimator of the type described above, in the case of which bending and deformation of the collimator plates at high speeds of the rotating part of the gantry are avoided as a consequence of the design according to at least one embodiment of the invention.

BRIEF DESCRIPTION OF THE DRAWINGS

Example embodiments of the invention are illustrated in the attached schematics, in which:

FIG. 3 shows a collimator according to the prior art,

FIG. 4 shows a collimator according to at least one embodiment of the invention.

DETAILED DESCRIPTION OF THE EXAMPLE EMBODIMENTS

Figure 1:
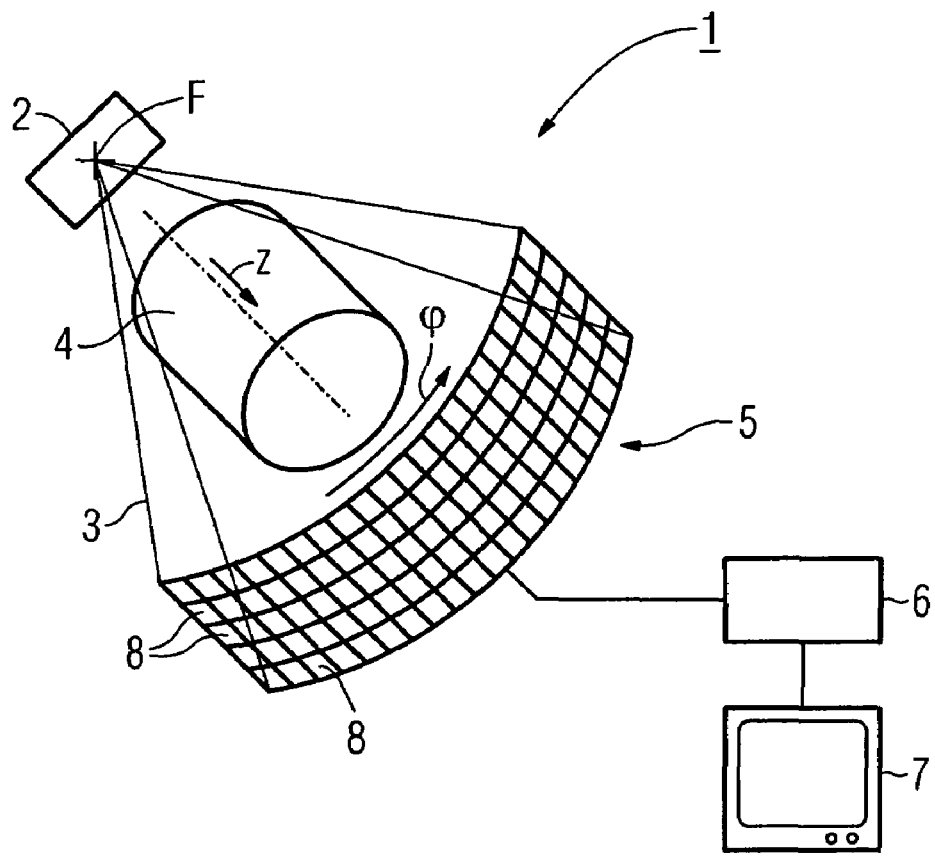
FIG. 1 is a schematic, in part block diagram of a computed tomography unit.

FIG. 1 shows a schematic, in part block diagram of a computed tomography unit 1. The computed tomography unit 1 includes an X-ray source 2 from whose focus F there emanates an X-ray beam 3, which is formed in a fan-shaped or pyramidal fashion, for example, by diaphragms that are not illustrated in FIG. 1 but are known per se. The X-ray beam 3 penetrates an object 4 that is to be examined, and impinges on an X-ray detector 5. The X-ray source 2 and the X-ray detector 5 are arranged, in a way not illustrated in FIG. 1, situated opposite one another on a rotary frame of the computed tomography unit 1, which rotary frame can be rotated in the f-direction about the system axis Z of the computed tomography unit 1.

During operation of the computed tomography unit 1, the X-ray source 2 arranged on the rotary frame and the X-ray detector 5 rotate about the object 4, X-ray pictures of the object 4 being obtained from different projection directions. Here, with each projection X-radiation that has passed through the object 4 and been attenuated by its passage through the object 4 impinges on the X-ray detector 5, the X-ray detector 5 generating signals that correspond to the intensity of the impinging X-radiation. Subsequently, an image computer 6 uses the signals determined by the X-ray detector 5 in order to calculate, in a known way, one or more two- or three-dimensional images of the object 4 that can be displayed on a display device 7.

In the case of the present example embodiment, the X-ray detector 5 has a multiplicity of detector modules 8 that are juxtaposed in the f-direction and in the z-direction on a detector arc (not illustrated in more detail) fastened on the rotary frame and form the planar X-ray detector 5 in the case of the present example embodiment.

Figure 2:
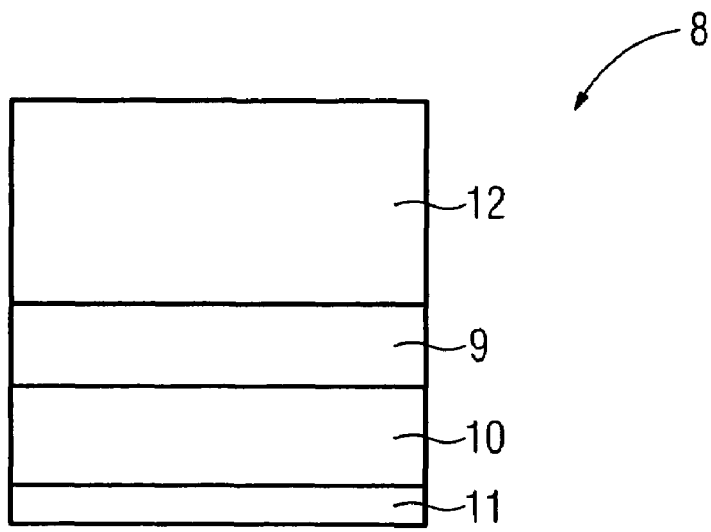
FIG. 2 shows a detector module of the computed tomography unit from FIG. 1.

A detector module of the X-ray detector 5 is illustrated by way of example in FIG. 2 in a greatly simplified way. In the case of the present example embodiment, the detector module 8 includes a scintillator array 9 that is arranged over a photodiode array 10. The photodiode array 10 is arranged, in turn, on a printed circuit board 11 that is shown only in part and on which electrotechnical components for processing the electrical signals produced with the aid of the scintillator array 9 and the photodiode array 10 are present in a way not illustrated in more detail.

The scintillator array 9 is structured and consequently includes a multiplicity of scintillator elements (not illustrated in more detail) that are respectively assigned to a photodiode of the photodiode array 10 including a multiplicity of photodiodes. The scintillator array 9 and the photodiode array 10 are mutually aligned and bonded to one another. The scintillator array 9 and the photodiode array 10 thus form an array of detector elements for X-radiation, a detector element having a scintillator element and a photodiode.

Instead of the scintillator array and the photodiode array, the detector module can, however, also have an array of detector elements that are made from a semiconductor material that converts X-radiation directly. X-radiation impinging on such detector elements is then converted directly into electrical signals that are further processed with the aid of the downstream evaluation electronics. Whatever the design of the detector elements of the detector module, each detector module has a collimator 12 that is arranged relative to the detector elements in such a way that only X-radiation of a specific spatial direction can strike the detector elements. The collimator 12 in this case has the function of preventing X-radiation that negatively influences imaging, that is to say, for example, X-radiation that has been scattered at objects, from striking the detector elements.

The collimator 12 has a multiplicity of juxtaposed thin collimator plates. The collimator plates may be made, for example, from tungsten, molybdenum, tantalum, or from an alloy containing one of these metals.

A collimator 30 according to the prior art is illustrated in FIG. 3. The collimator 30 according to the prior art has a cover element 31 on its top side and a base element 32 on its underside, in which the juxtaposed plates 33 of the collimator 30 are positioned relative to one another and fixed. The cover element 31 and the base element 32 are plastic parts. The space between the collimator plates 33 is filled with air. For this reason, when used in a computed tomography unit the collimator plates 33 are bent as a consequence of the forces acting on them. This bending or deformation of the collimator plates can go so far that they cast an X-ray shadow during examination of an object, and therefore lead to image defects.

In order to prevent the collimator plates, in particular of a collimator that is located at the edge of the detector arc of the computed tomography unit 1, from bending or being deformed as a consequence of forces acting as the rotary frame rotates about the object 4, it is proposed according to at least one embodiment of the invention to arrange between the collimator plates supporting elements that laterally support the collimator plates and thereby prevent deformation of the collimator plates as the rotary frame of the computed tomography unit 1 rotates about the object 4.

An inventive collimator 12 having such supporting elements 13 is illustrated in FIG. 4. The collimator 12 has a base element 14 provided with supporting elements 13, and a cover element 15 provided with supporting elements 13. The base element 14 of the collimator 12 from FIG. 4 is illustrated in more detail in FIG. 5.

Figure 5:
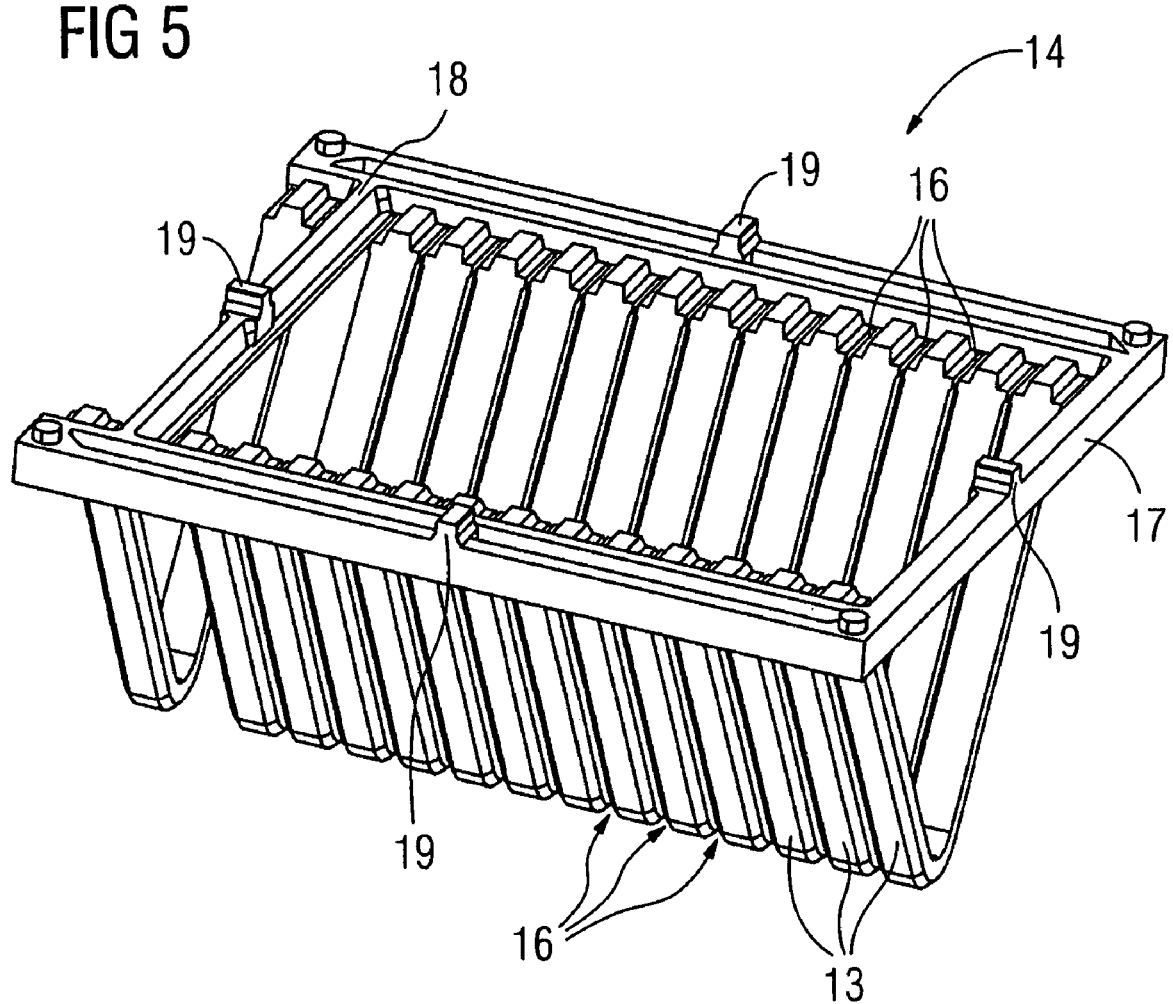
FIG. 5 shows the base element of the collimator from FIG. 4, and FIGS. 6 to 8 show alternative design shapes of supporting elements.

As is to be seen from FIG. 5, the base element 14 comprises a number of juxtaposed V-shaped supporting elements 13 that are interconnected in such a way that slots 16 are located between the supporting elements 13, a slot 16 being provided in each case for holding a collimator plate 20. In order to stiffen the base element 14, the latter has a support strut 17 arranged at the edge and a support strut 18 arranged between 2 supporting elements 13.

Moreover, in the case of the present exemplary embodiment, the base element 14 is provided with four positioning lugs 19 in order to be able to arrange the collimator 12 by means of the positioning lugs 19 in an accurately positioned fashion over a scintillator array 9 of the X-ray detector 5. In order to construct the collimator 12, the collimator plates 20 are inserted into the slots 16 of the base element 14 and into the slots 16 of the cover element 15 (of substantially identical design) such that the collimator 12 illustrated in FIG. 4 results. The collimator plates 20 are bonded here, for additional stiffening, to the supporting elements 13 of the base element 14 and the cover element 15, a low-viscosity adhesive being used to this end.

The base element 14 and the cover element 15 may be made, for example, from a glass fiber reinforced liquid crystal polymer. Both the base element 14 and the cover element 15 may be, for example, an apparatus fabricated using injection molding technology.

Figure 6:
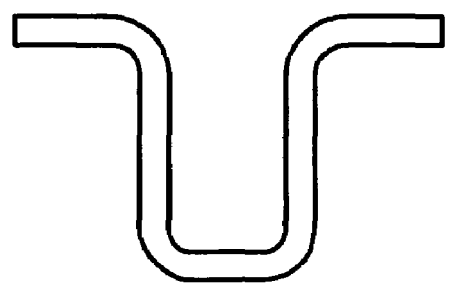
Figure 7:
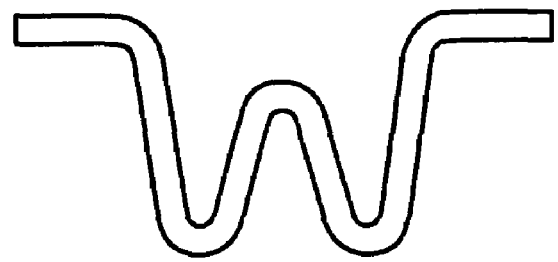
Figure 8:
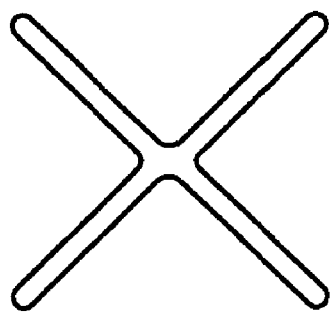

As an alternative to the V-shaped design, shown in FIGS. 4 and 5, of the supporting elements 13, it is also possible to design the supporting elements in U-shaped or W-shaped fashion as is illustrated in FIGS. 6 and 7. Moreover, it is also possible for supporting crosses, of which one is illustrated in FIG. 8, to be used as supporting elements. All of the respective identical designs of supporting elements can in this case be interconnected in such a way as to result in an apparatus comparable to that shown in FIG. 5 and provided with slots and which can serve as base element or cover element for the collimator.

However, it is also alternatively possible to construct the collimator according to at least one embodiment of the invention by using a type of stacking technique in which the supporting elements are not interconnected. In this case, a collimator plate and a supporting element, for example a supporting cross, are alternately stacked and bonded to one another. This process is continued until a collimator of appropriate dimensions is obtained.

Irrespective of the embodiment of the supporting elements, the supporting elements or the apparatus including the supporting elements exhibits at least substantially the same wall thickness, particularly in the direction of the X-radiation penetrating them, such that the attenuation, which is certainly extremely slight, but present nevertheless, of the X-radiation by the supporting elements or the apparatus is always substantially the same, and thereby no image defects are produced.

The collimator according to at least one embodiment of the invention certainly may be, for example, provided for a computed tomography unit. However, the use of the collimator according to the invention is not restricted to computed tomography units. Rather, the collimator can also be used in other tomography units.

Instead of the material, it is also possible to use other materials transparent to X-rays for the supporting elements. The same holds true for the adhesive and for the materials provided for the collimator plates.

Furthermore, it is also possible to conceive other shapes than the shapes described above for the supporting elements for the lateral support of the collimator plates.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A collimator for a beam detector, comprising:
   at least two juxtaposed collimator plates; and
   at least one supporting element, arranged between at least two juxtaposed collimator plates, for stiffening the collimator, the at least one supporting element being constructed from a material transparent to X-rays and supporting the collimator plates laterally.

2. The collimator as claimed in claim 1, wherein the collimator includes at least two supporting elements, interconnected in such a way that the collimator includes a device including slots between the supporting elements, each one slot being provided for holding a collimator plate.

3. The collimator as claimed in claim 2, wherein the collimator includes two devices with slots between the supporting elements for holding collimator plates, in which one device serves as a base element and the other device serves as a cover element.

4. The collimator as claimed in claim 2, wherein the slots are configured in such a way that, in the event of arrangement over a beam detector, the collimator plates arranged in the slots are aligned at least substantially with a focus of a radiation source assigned to the beam detector.

5. The collimator as claimed in claim 1, wherein the supporting elements are designed as supporting crosses.

6. The collimator as claimed in claim 1, wherein the supporting elements are of at least one of U-, V- and W-shaped design.

7. The collimator as claimed in claim 1, wherein the supporting elements include at least substantially the same wall thickness.

8. The collimator as claimed in claim 1, wherein the supporting elements are made from a glass fiber reinforced liquid crystal polymer.

9. The collimator as claimed in claim 2, wherein the device having slots is an injection-molded part.

10. The collimator as claimed in claim 2, wherein the device having slots includes a support strut at least one of on the edge side and arranged between two supporting elements.

11. The collimator as claimed in claim 1, wherein the supporting elements are bonded to the collimator plates.

12. The collimator as claimed in claim 11, wherein the adhesive is a low-viscosity adhesive.

13. The collimator as claimed in claim 3, wherein the base element includes at least one positioning lug for the purpose of positionally accurate arrangement over a beam detector.

14. The collimator as claimed in claim 1, wherein the collimator plates include at least one of tungsten, molybdenum and tantalum.

15. An X-ray detector, comprising the collimator as claimed in claim 1.

16. The collimator as claimed in claim 1, wherein the collimator is alignable on all sides next to collimators of identical design.

17. A computed tomography unit comprising a collimator as claimed in claim 1.

18. The collimator as claimed in claim 3, wherein the slots are configured in such a way that, in the event of arrangement over a beam detector, the collimator plates arranged in the slots are aligned at least substantially with a focus of a radiation source assigned to the beam detector.

19. An X-ray detector, comprising the collimator as claimed in claim 2.

20. A computed tomography unit, comprising a plurality of collimators as claimed in claim 1, each aligned on all sides next to collimators of identical design.

* * * * *